United States Patent [19]

Schneider

[11] Patent Number: 5,279,971

[45] Date of Patent: * Jan. 18, 1994

[54] METHOD FOR DETERMINING A BINDER CONTENT OF BITUMINOUS BUILDING MATERIALS

[75] Inventor: Ulrich Schneider, Lohfelden, Fed. Rep. of Germany

[73] Assignee: Hermann Riede Strassen-U. Tiefbau GmbH U. Co. KG, Kassel, Fed. Rep. of Germany

[*] Notice: The portion of the term of this patent subsequent to Jan. 14, 2009 has been disclaimed.

[21] Appl. No.: 771,448

[22] Filed: Oct. 4, 1991

Related U.S. Application Data

[63] Continuation-in-part of Ser. No. 324,017, Mar. 16, 1989, Pat. No. 5,081,046.

[30] Foreign Application Priority Data

Mar. 17, 1988 [DE] Fed. Rep. of Germany ....... 3808888

[51] Int. Cl.$^5$ .............................................. G01N 5/04
[52] U.S. Cl. ................................ 436/139; 73/61.46; 208/41; 436/155; 436/160
[58] Field of Search ............... 436/139, 145, 155, 177, 436/181, 160; 422/51, 68; 73/866, 61.3; 208/6, 41, 42

[56] References Cited

U.S. PATENT DOCUMENTS

| 1,967,424 | 7/1934 | Nevitt | 73/61.77 |
| 2,679,159 | 5/1954 | Messer | 73/38 |
| 3,453,083 | 4/1966 | Beerli | 422/270 |
| 4,054,506 | 10/1977 | Hart et al. | 208/11 |
| 4,412,007 | 10/1983 | Yong et al. | 436/139 |
| 5,081,046 | 1/1992 | Schneider | 436/139 |

OTHER PUBLICATIONS

Encyclopedia of Polymer Science and Technology: Plastics, Resins, Rubbers, Fibers vol. 14, 1971 by John Wiley & Sons, Inc. pp. 1-5.

Primary Examiner—James C. Housel
Assistant Examiner—Ramon Torres
Attorney, Agent, or Firm—Michael J. Striker

[57] ABSTRACT

A method of determining the binder content of bituminous building material including a mixture of a mineralic constituent, a bituminous binder and moisture comprises the steps of: preparing a sample of the material, heating the sample to a temperature between 300° to 550° C. to thermally remove the moisture and the binder without substantially decomposing the other constituents of the mixture, cooling the sample to ambient temperature after the thermal removal of the binder and before subsequently weighing the sample, generating during the heating step a curve which reflects total weight loss of the sample in relation to time, ending the heating step when the curve shows that removal of the moisture and decomposition of the binder has substantially ended, taking from the curve a break point which shows up to which time the weight loss is substantially due to the removal of moisture from the sample and from which time the weight loss is substantially due to a decomposition of the binder, determining the binder content of the sample from the difference between the total weight loss of the sample and the weight loss of the sample at the break point.

5 Claims, 3 Drawing Sheets

METHOD FOR DETERMINING A BINDER CONTENT OF BITUMINOUS BUILDING MATERIALS

CROSS-REFERENCE TO RELATED A APPLICATION

This application is a continuation-in-part of application Ser. No. 324,017 filed on Mar. 16, 1989, now U.S. Pat. No. 5,081,046.

BACKGROUND OF THE INVENTION

The invention relates to a method and an apparatus for determining the binder content of bituminous building materials, especially asphalts, wherein a sample of the building material is weighed, the binder is removed from the sample, the sample is reweighed, and the binder content is determined from the weight loss of the sample due to removal of the binder.

The development of such methods is a result of the scarcity of raw materials which has been constantly increasing in recent times, and of the often great amount of unusuable scrap material. In road building there has often been a call for reusing old paving material in the improvement of old pavements or in the production of new pavements, for example by adding to the usual fresh mixtures of rock (e.g., basalt, sand or the like), additive materials or fillers (e.g., limestone) and binders (pure bitumen, as a rule), and preparing hot asphalt concrete together with them in a special drying and mixing apparatus (DE-OS 3,616,995).

A bituminous material made by adding old material must satisfy the same quality requirements as one made without the addition of old material. To be able to satisfy these requirements it is necessary to know the composition of the old material as regards its binder content, the grain size distribution and the content of additives, since only then can the proportions of the fresh starting materials on the one hand and of the old material on the other be precisely controlled.

In one known method of the kind described above, the removal of the binding agent from the sample is performed by extraction with a solvent. The time required for such analysis is quite long, and is unacceptable, especially for the analysis of large samples of about one to five kilograms. Besides, the use of solvents is undesirable for environmental reasons. If the analysis of the binder content, however, is performed using a neutron probe in the likewise-known isotope determination, the binder content can indeed be determined in a very short time. Unlike the extraction method, however, isotope determination does not result in any automatic separation of the binding agent from the rest of the mineral mix. Therefore the removal of the binder must be performed in an additional step which considerably adds to the total analysis time, since otherwise the next-following sieve analysis of the rock mixture to determine the grain-size distribution, which cannot be performed prior to the separation of the binder component, would not be possible. Also, problems would arise in case the determination of the content of additives would have to be performed, for example, by sedimentation.

SUMMARY OF THE INVENTION

It is therefore the aim of the invention to improve the method described above such that it will permit the processing of samples of relatively great mass in a comparatively short time and nevertheless permit separation of the binder from the rest of the material mixture consisting of rock and sometimes additives. Another aim is to create an apparatus suitable for the practice of the method, by means of which the binder content of the sample can be determined in a simple manner.

For the achievement of this aim provision is made in accordance with the invention to perform the removal of the binder from the sample by thermal degradation.

The invention is based on the knowledge that bitumen or bitumenous binders, which are contained in various materials, especially paving materials, consist of organic components which can be removed from samples of the material by heating the latter. This removal of the bituminous component, referred to generally hereinafter as "thermal degradation," can be referred to as combustion in the presence of oxygen, on the one hand, and on the other hand as thermal decomposition in the absence of oxygen. In practical applications, both kinds of degradation may be involved. Furthermore, the invention is based on the knowledge that characteristic temperature ranges exist in which, if they are maintained, only the bituminous component of the said paving material is decomposed or burned, and, if the thermal degradation is continued for sufficient time, it is removed entirely from the starting material, so that the weight loss of the samples due to this is a direct measure of their original binder content. At the same time the advantage is obtained that the rest of the components of the paving materials here involved are neither decomposed or burned or in any other way adversely affected, so that the analysis of the remaining components in the conventional ways offers no difficulty whatever after the removal of the binder component.

Moreover, the invention offers the advantage that samples weighing approximately one to five kilograms can be completely freed of the binder by thermal degradation of the latter within fifteen to thirty minutes.

The invention will be further explained below by embodiments in conjunction with the appended drawing, wherein:

DESCRIPTION OF THE PREFERRED EMBODIMENTS

Figure 1:
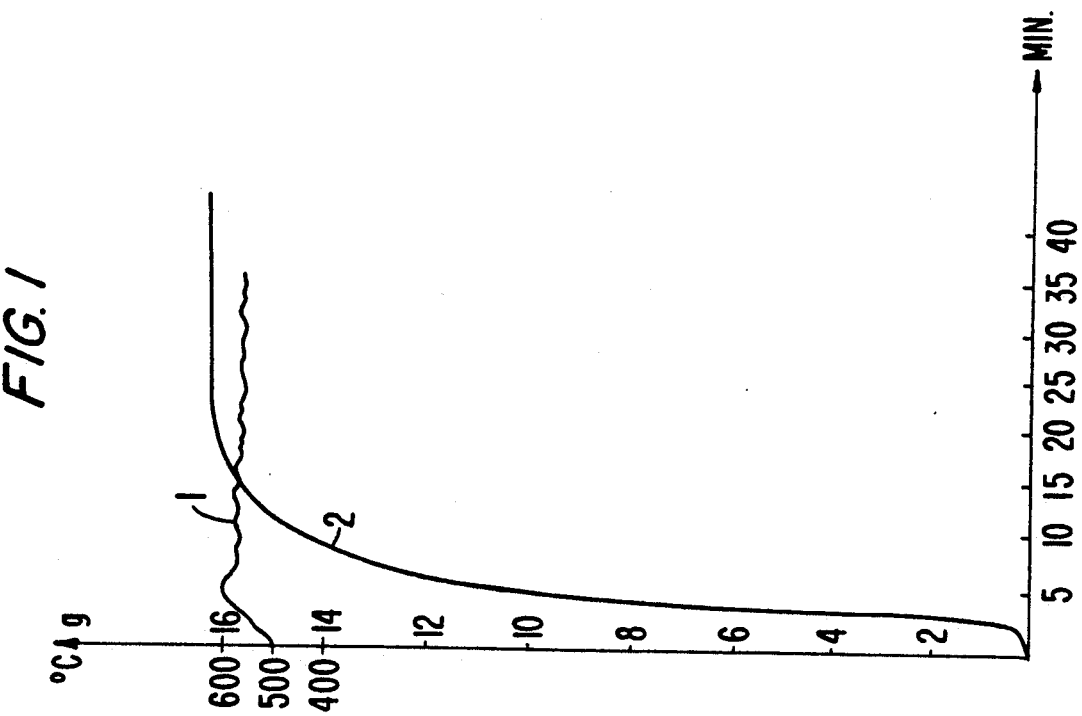
FIG. 1 is a graphic representation of the weight loss of a sample of bituminous paving material by thermal degradation of the binder after sufficient preliminary drying of the sample.

FIG. 1 shows graphically the course of the thermal degradation of the binder on the example of a sample of 299.8 g of ground asphalt. The sample was first predried in the usual manner for at least one day at about 105° C. to remove the moisture content. Then the sample was exposed to an average temperature of about 550° C. in an electrically heated oven. The duration of the heat treatment is recorded in minutes along the abscissa in FIG. 1, while the measured weight loss of the sample is given in grams along the right side of the ordinates and the temperature prevailing in the oven is given along the left side. The wavy temperature curve represented at 1 is a result of the conventional temperature control, which leads to temperature fluctuations between preselected minima and maxima.

The weight loss of the sample represented by curve 2 shows that only a very slight weight loss occurs within the first three to four minutes. Accordingly, the weight loss of the sample produced by the incipient decomposition or combustion of the bituminous binder increases steeply for a period of up to about twenty minutes, while after that virtually no increase in the weight loss can be observed. It can be concluded from this that, after about twenty to twenty-five minutes, all of the binder contained in the sample is decomposed or burned and removed from the sample, so that the thermal degradation can be considered complete after twenty-five minutes. The analysis of the binder content takes in this example no more than about half of the time that would be required by the known analysis by extraction. The weight loss of the sample in the example represented amounts to 16.3 g, which corresponds to a binder content of about 5.44 wt.-% in the starting sample.

In addition to the more rapid removal of the binder from the sample, the method of the invention offers the additional advantage that the remainder of the specimen after the thermal degradation of the binder, in contrast to the extraction process, is completely dry on account of the previous heating, and therefore can be subjected immediately to a sieve analysis, resulting in a further reduction of the time required for the complete analysis. It is advantageous to subject the remaining mineral mixture to the sieve analysis, not while it is hot, but after a certain cooling performed preferably to the ambient temperature, so as to prevent the grains from sticking together or adhering too tightly to one another or to the sieves and thereby affecting the sifting process and especially the sifting rate. No impairment of the sieve analysis by the preceding thermal degradation of the bitumen or bituminous binder has been as yet observed. In case of necessity, a determination of the content of additives can be made in addition to the sieve analysis, if such determination cannot be performed also by screening.

In the analysis of samples of a precisely known binder content, it has further been found that the temperatures commonly used previously in predrying, of about 105° C., are too low to evaporate all of the moisture contained in the sample, even if the predrying is performed over several days. Therefore it is proposed in accordance to the invention to perform the predrying at higher temperatures, preferably at 200° to 300° C. After such temperatures were applied for 24 hours, for example, no marked weight losses that could be attributed to the removal of residual moisture could be observed during the thermal degradation of the binding agent. This is possibly to be attributed to the fact that, at 105° C., substantially only the surface moisture is evaporated, while at higher temperatures the moisture that is in the pores is released.

In the thermal degradation of the binding agent a temperature of about 550° C. should not be exceeded, since at about 600° C. a decomposition of limestone begins, which is added to many paving materials of the kind herein concerned as an additive or filler. Especially at temperatures around 900° C., additional weight losses occur which can be attributed only to the decomposition of limestone to calcium oxide and carbon dioxide. In the case of the decomposition of the limestone or of any other additive which takes place parallel to the thermal degradation of the binder, then both the measurement of the weight loss of the sample, performed to determine the binder content, and any later sedimentation performed to determine the additives content, would lead to inaccurate results. Therefore it is proposed in accordance with the invention to perform the thermal degradation of the binder at temperatures up to no more than 550° C,, so that on the one hand the binder will be completely removed from the sample, and on the other hand the limestone can be left unaltered in the sample.

Particularly good conditions will result if the predrying is performed at a temperature between 105° and 300° C. and the thermal degradation of the binder is performed at a temperature between 300° and 550° C. The assurance is thus given in the predrying that, in spite of an improved drying action, the binder content will be completely preserved, whereas during the thermal degradation only the binder, not the limestone or other additives, will be wholly or partially removed from the sample. The duration of the predrying can thus be reduced to about three hours, since after this time about 90 wt-% of the moisture content has already been removed, and therefore there will be no more than a slight error in the binder content, which can be accepted.

To accelerate the above-described method of analysis it has proven to be desirable to pass air, air enriched with oxygen, or pure oxygen over the sample during the thermal degradation of the binding agent, which can be accomplished by means of an on-site air compressor or with the aid of bottled oxygen. To prevent any cooling of the oven or sample temperature by the entering cold gas it is advantageous to warm it to the temperature of the oven interior before introducing it into the oven, thereby virtually excluding any delaying of the thermal degradation of the binder due to heat loss. In addition, the preheating of the air or oxygen presents the advantage that very large sample grains, especially grains of basalt, will not be shattered by abruptly occurring thermal tensions, which might result in a change of the grain-size distribution of the minerals in comparison to the original sample.

The air or the oxygen is best passed over the sample at a defined rate. If air is used, an air feed rate of 400 to 600 l/h has proven to be especially desirable for samples up to about 1 kg. With such air feed rates the period of time needed for the complete removal of the binder from the sample by thermal degradation can be reduced to about half of that required for thermal degradation without air feed. At air feed rates between 100 and 1,000 l/h, a minimum was found for the period of time needed for removing the binder from the sample. At low feed rates or greater feed rates, longer analysis times were the result. In the case of samples over about 1 kg, air feed rates of up to 1,500 l/h may be desirable.

Another means for reducing the time required for thermal degradation is to spread the sample placed in the oven over as large an area as possible. If this is not possible for lack of space, it is desirable to supply mechanical energy to the sample during the thermal degradation by subjecting it or the vessel containing it to a slight shaking or stirring process, for example, if it is performed so gently as not to produce any change in the grain size distribution. In this manner the advantage is obtained that, during the thermal degradation of the binder, all parts of the sample can be exposed directly to the air or additional amounts of air or oxygen can reach all areas of the sample.

Figure 2:
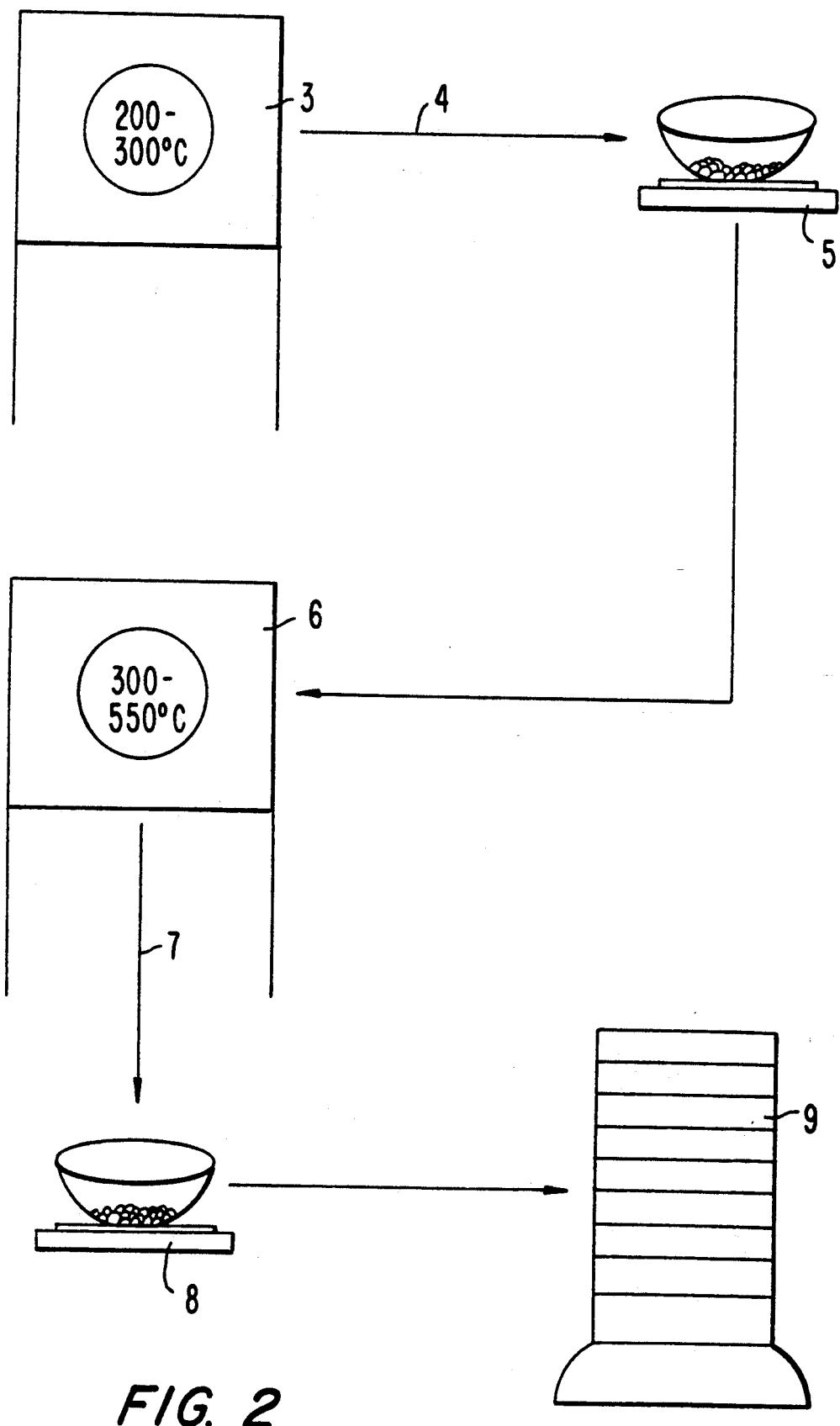
FIG. 2 is a diagrammatic representation of the individual steps in the practice of the method of the invention.

The individual steps performed in the method of the invention are represented diagrammatically in FIG. 2. An oven 3 is used for the predrying of the sample, being operated at an internal temperature of 200° to 300° C. After removal from the oven 3 the sample is subjected to cooling indicated by an arrow 4, which can best result in cooling to the ambient temperature so as to avoid affecting the next-following first weighing of the sample by means of a scale 5. After weighing, the binder container in the sample is subjected to thermal degradation in an oven 6 and thereby completely removed from the sample. Then the remainder of the sample is cooled again to the ambient or room temperature, as indicated by an arrow 7, and then is weighed again on another scale 8 or also in scale 5. After the second weighing the remainder of the sample can be subjected to a sieve analysis in a sifting device 9 consisting of several sieves of different mesh size.

Alternatively, it would be possible to treat the sample in a mixing and conveying drum with an inclined axis, heated externally by electricity, to which the sample as well as air or oxygen are fed through the one end wall, while the other end wall serves for the removal of the treated sample. The time of stay of the sample in the mixing drum can be established by the rotatory speed for a given inclination of the axis. By the additional creation of ribs or paddles on the inside of the drum jacket, the sample can be kept in constant movement during the treatment, so that the entire surface of the sample can be reached by the air or oxygen.

So that not every sample will have to be observed in the procedure described above, to see whether the binder has already been completely removed, the samples are best kept for a period of time at the temperature selected for the thermal degradation, which will be slightly longer than the maximum period of time that has been determined for the accomplishment of the complete removal of the binder from a number of different samples. In this manner it is possible to fix the time of stay of the samples in the apparatus that is used in the individual case. The same method can be applied to the predrying.

Figure 3:
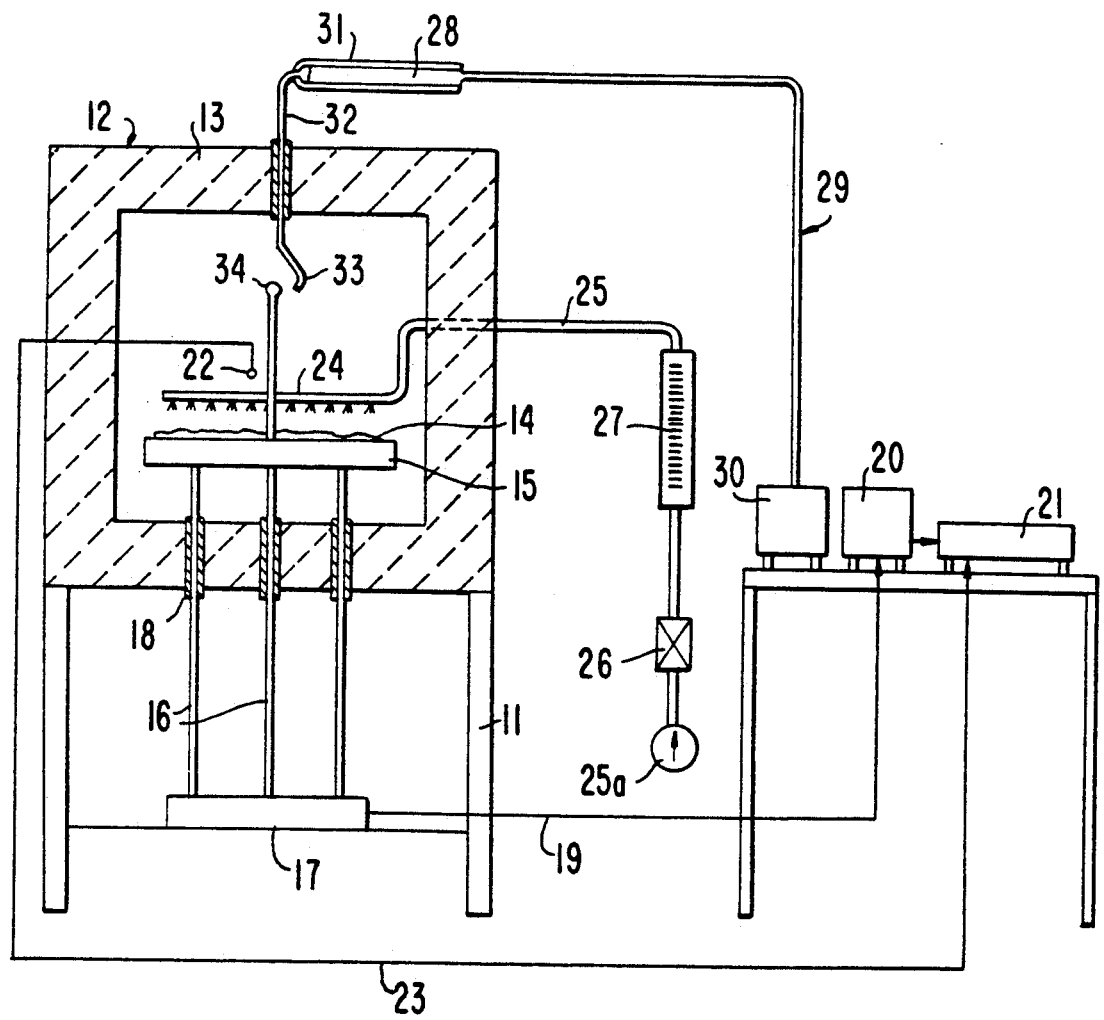
FIG. 3 shows an apparatus for the largely automatic practice of the method according to the invention.

In a preferred embodiment, the method of the invention including the predrying can be performed largely automatically with an apparatus in accordance with FIG. 3. The apparatus contains an oven 12 supported on a frame 11 and having a completely closed housing 13 which has a door, not shown, for the insertion and for the removal of samples 14. In the housing 13 there is a container 15 which preferably consists of a metal mesh, basket or grid which is stable at high temperatures, so that the inserted sample 14 can be gradually heated and ventilated on all sides. Alternatively it would be possible to provide a box-like container of high-grade steel or the like and pack the sample in a wire mesh or the like. The container 15 is supported on legs 16 whose upper ends extend into the interior of the housing 13 and whose bottom ends are fastened on the weighting platform or tray of a scale 17, and whose midsections are mounted for sliding in bushes 18 consisting of refractory and heat blocking material. These bushes 18 are fixed in vertical bores in the floor of the housing 13. In this design the upper ends of the legs 16 form a support for the scale 17 for the container 15. Therefore it is possible constantly to study the weight of the sample 14 placed in the container and read any weight losses directly on the dial of the scale 17.

The scale 17 is preferably one with an electrical or electronic display in which the signal produced by an expansion strip or an electromagnet or the like is delivered to an output intended for the remote display of the result of the weighing. This output is connected by an electrical conductor 19 to a digital-to-analog converter 20 which converts the digital signal to an analog signal and delivers it to an output which is connected to the corresponding terminal of an electrically controlled x/t recording apparatus 21 which serves for the automatic analog recording of the weights measured by the scale 17 in relation to time. The recording apparatus 21, which can be a conventional pen recorder, a graphics-capable printer or plotter or even an oscillograph or the like, is preferably a multiple recording instrument with at least two switchable or parallel-operating measuring points, so that at least two magnitudes can be recorded alternately in succession or parallelly. In the embodiment a dual recorded is provided to whose one measuring points are fed the signals coming from the analog-to-digital converter.

Within the oven 12, those temperature can be controlled, a temperature sensor 22, e.g., a thermocouple, is disposed just above the container 15, and its output signal is fed through an electrical conductor 23 passing insulated through the housing 13 to an additional measuring point of the recording apparatus 21. The temperature sensor 22 serves to measure continuously the temperature actually prevailing in the vicinity of the sample 14, while the recording instrument 21 performs the task of recording this temperature analogously and step-wise or continuously.

Just above the container 15 there is furthermore a tube 24 with a plurality of openings facing the container 15 and serving for the introduction of air; it is connected by a tube 25 passed insulated through the housing 13 to a compressed-air connection 25a, an oxygen source or the like. Also, a control valve 26 for adjusting the rate of feed of the gas and a flow meter 27 for determining the actual rate of flow, are inserted advantageously into the tube 25. The tube 25 can be coiled helically outside of the container 15 and can be jacketed with a heating means, not shown, to heat the gas, before it enters the container 15, to the interior temperature of the latter. Lastly, a camshaft 28 is disposed above the container 15 and can be rotated through a diagrammatically indicated gearing 29, a shaft or the like, by an electric motor 30. On the camshaft 28 is mounted a sleeve 31 which bears, on a linkage 32 brought insulated through the housing 13, a coupling 33 which if necessary can be coupled to a coupling means 34 of the container 15 in order to impart a slow shaking movement to the latter during the analysis. The coupling 33 consists, for example, of a hook which can be hung in an eye on the container 15 and then can be lifted together with the latter.

The process in accordance with the invention is performed by the use of the apparatus of FIG. 3 in the following manner:

The sample 14 is placed in the oven 12 at a relatively low oven temperature of, for example, about 100° C., so that the temperature within the container 15 continuously rises to about 550° C. and then fluctuates about this level. The precise temperature is controlled by means of the temperature sensor 22. At the same time the weight loss of the sample 14 is continuously determined by means of the scale 17. Both steps can be done continuously or step-wise. Since the weight loss no longer varies after the sample 14 has been in the container 15 for about 20 to 25 minutes, it can be assumed that the thermal degradation of the binder is complete after this period of time.

Figure 4:
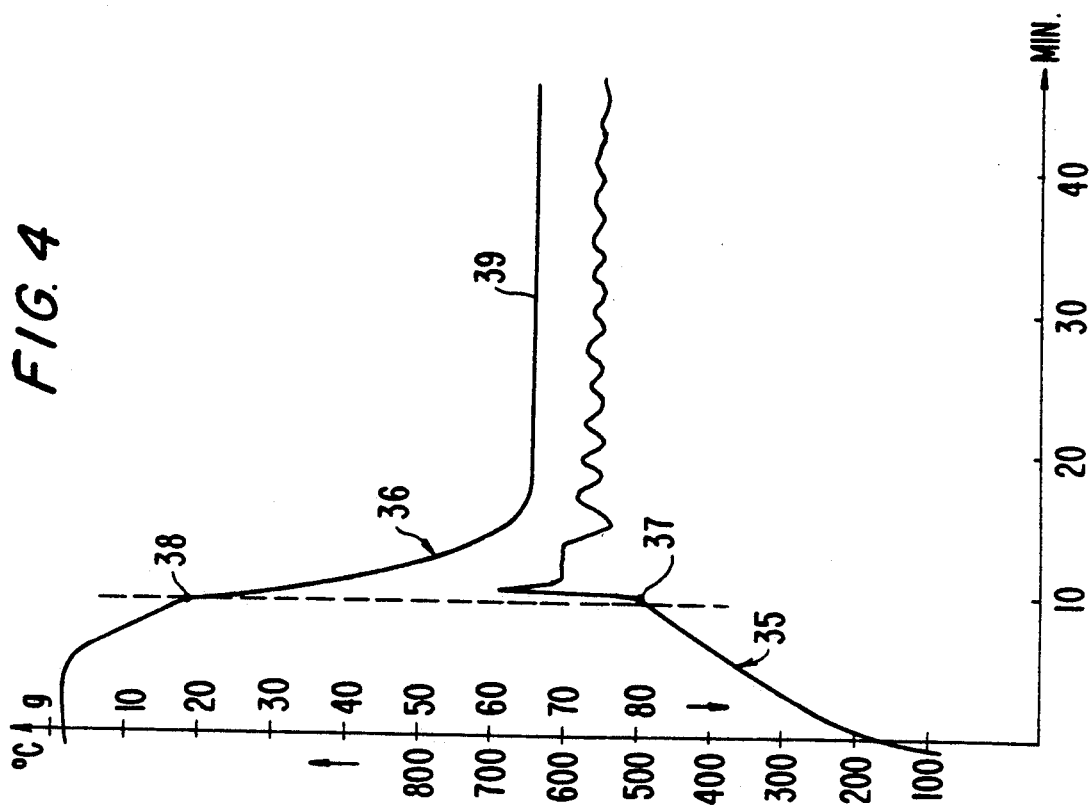
FIG. 4 is an additional graph of the weight loss of a sample of bituminous paving material by the technical degradation of the binding agent, wherein the method of the invention is largely automatic.

Special advantages result from the use of the recording instrument 21. In FIG. 4 the recording of the analysis made with a conventional dual recorder is represented. In a Cartesian system of coordinates, the time in minutes is recorded on the abscissa corresponding to the velocity provided for the paper advance or the like of the recording instrument 21, while on the left of the ordinates is recorded the temperature at the temperature sensor 22 and on the right (from the top down) the weight loss of the sample 14, which is referred to the initial weight of the sample 14 upon its introduction into the container 15.

As FIG. 4 shows, both a curve 35 representing the temperature and a curve 36 reflecting the weight loss have a characteristic break 37 and 38, respectively. The break 37 is attributed to the fact that the temperature at the location of the temperature sensor 22 at first rises comparatively slowly, and during this time any water or the like that might still be in the sample 14 is evaporated. But as soon as the water is removed from the sample 14 (break 37), evidently a burning of the binder takes place abruptly, thereby abruptly and briefly raising the temperature at the location of the temperature sensor 22 disposed just above the sample 14, even above the level of 550° C. that is desired, and shortly thereafter dropping it back to the level of about 550° C. This rising of the temperature might be due to the fact that the temperature sensor 22 is at least temporarily disposed within the flame of the binder and thus senses a higher temperature as compared with a location outside the flame. The upper temperature limit is, however, not exceeded by an amount and for a length of time such that an essential undesired decomposition of limestone or other additives could occur. On the other hand the break 38 is attributed to the fact that the weight loss occurring up to the break is to be attributed mainly to the comparatively slow loss of moisture, while at the break 38 the abrupt thermal decomposition of the binder takes place, resulting in a comparatively rapid and likewise abruptly occurring weight loss of the sample. All measurements performed with the apparatus of FIG. 3 have surprisingly shown that the two breaks 37 and 38 of all samples coincide at the same abscissa, and that the relative positions of these breaks in the coordinate system depend, among other things, on the kind of quality of the samples 14, the sample weight, and the particular experimental circumstances.

What is especially important for the practical and economical application of the method of the invention is the fact that the break 38 can be considered as the point at which the removal of the moisture from the sample is largely completed and the thermal decomposition of the binder substantially begins. Therefore the portion of the weight loss caused by the decomposition of the binder, and hence also the binder content of the sample, are computed from the difference between the weight loss measured at the break 38 and the weight loss which is obtained in the area 39 of curve 36 reached at the end of the decomposition, and changes virtually not at all even if the temperature of about 550° C. is long sustained. The same would be true if the sample, after its weight loss has reached the area 39 of curve 36, is cooled again to the ambient or room temperature before the final weighing step and before removing the sample from the oven 12 and subjecting it to the subsequent sieve analysis as has been described above with respect to the other embodiment (see page 13, third paragraph). Since the weight loss at break 38 in FIG. 4 is about 18 g, and in area 39 it is about 65 g, the binder content in the sample can be computed at approximately 47 g.

An especially preferred variant of the method of the invention thus consists in recording at least curve 36 indicating the progress of the weight loss, doing so continuously or step-wise during the heating of the sample 14 in the oven 12, and, when area 39 of curve 36 is reached, determining the weight loss due to the decomposition of the binder from the above-mentioned difference. Numerous tests with different kinds of samples which contained a known content of binder have shown that the binder contents determined by the method shown in FIG. 4 correspond to the known binder contents with the accuracy necessary for practical purposes. An important advantage is that the samples 14 do not have to be subjected to any predrying, and that nevertheless the desired binder contents are available as soon as area 39 of curve 36 is reached. Thus the results are immediately available, regardless of the nature and amount of the sample 14, upon the completion of the thermal decomposition of the binder, i.e., at the soonest possible moment in each case.

For a rapid and accurate analysis it has been found desirable to dispose the temperature sensor 22 in the container 15 at a defined distance from the sample 14, because it has been found that this has a good influence on the definition of the break points 37 and 38. In the embodiment represented, a distance of the temperature sensor 22 from the sample 14 of about 15 cm has proven to be especially desirable.

To accelerate the thermal decomposition of the binder, air can be supplied during the analysis at the stated rates of feed, which can be controlled by the valve 26. It has been found desirable to use a container 15 of a size of about 30 cm × 30 cm, and a toroidal tube 24 disposed above it and having holes of a diameter of 1–2 mm and a distance of about 30 mm, in order to distribute the air stream uniformly over the entire sample and thereby effectively accelerate the decomposition of the binder. At the free end of the tube 24 is best closed air-tight so that the air can issue only in the direction of the sample 14.

It is furthermore possible to supply mechanical energy to the sample at one or more points by connecting the couplings 33 and 34 together and turning on the shaking device 28–32. The shaking action can as a rule be limited to brief phases of several seconds during the decomposition of the binder in order to accelerate its complete removal from the sample and to reach portion 39 of curve 36. For this purpose it is desirable to make the actual sample holder of a screen or mesh or the like, and to dispose beneath it a tray on the scale 17 so that the material freed from binder will be able to fall, while the shaking is in progress, onto the tray and thus be removed from the continued decomposition process. This will prevent such material from coating itself around the material particles still containing binder and thereby interfere with their decomposition.

Surprisingly, it has finally been found, and it is important to the practical application of the invention, that the weighing of the sample with the apparatus according to FIG. 3 suffices to determine the binder content with the necessary accuracy, i.e., the sample does not have to be additionally weighed before entering the oven 12 nor after its removal therefrom and complete cooling, even if this would be possible as mentioned above with respect to the other embodiment without departing from this invention. Therefore, after a sample has been removed from the oven 12 and cooled to about 100° and 200° C. the next analysis can immediately be started.

The invention is not limited to the embodiments described, which can be modified in many ways. The predrying in the procedure of FIGS. 1 and 2 could be performed by means of microwaves, for example. Furthermore, it is not necessary to treat all samples at the same temperatures and/or for equal time intervals if the procedure of FIGS. 3 and 4 is chosen. If the sample 14 in this case is already sufficiently predried, the curve 36 (FIG. 4) automatically changes to curve 2 (FIG. 1), i.e. no weight loss due to evaporation of water occurs and the missing break points 37, 38 show that all weight loss is due to binder decomposition. Of course it would also be possible to at least partially predry the sample in the oven 12 at a temperature of e.g. 200°-300° C. as described above (page 10, second paragraph, page 10, last paragraph, page 11, first paragraph) with respect to the other embodiment. In this case curves 35 and 36 would be similar to those of FIG. 4 with the difference that curves 35 and 36 would have portions associated to temperatures between 200 and 300° C. Besides, other designs can be provided which permit a continuous or step-by-step weighing of the sample 14 while it is being arranged in the oven 12.

WORKING EXAMPLES

1. A sample of ground asphalt was used, which had a known composition, and weighed 326.7 g, and which was made with a mineral mixture of basalt and sand as well as limestone as fillers, with bitumen as binder. The mineral mixture contained 30 wt.-% of grains of less than 2 mm diameter, 20 wt.-% grains of more than 16 mm diameter, and 50 wt.-% of grains of grain sizes between these two sizes. In accordance with the procedure of FIGS. 1 and 2, the sample was predried for several days at 105° C. and then treated in an oven at 500° C. After a treatment of twenty minutes the maximum weight loss was reached, which amounted to 13.2 g, corresponding to a binder and moisture content of 4.04 wt.-%. Comparative measurements with similar samples predried at 200° C. for the same period of time showed a weight loss of only 11.76 g, corresponding to a binder content of 3.6 wt.-%. From this it is found that the samples predried at 105° C. still contained a moisture residue of 1.44 g or 0.44 wt.-%. By the introduction of air into the oven at a rate of 600 l/h, the period of time required for the removal of the binder from the sample could be reduced by about 50% under otherwise the same conditions. The result of the analysis agreed precisely with the known composition of the ground asphalt analyzed.

2. A sample of fresh paving material (asphalt concrete) with an initial weight of 1,297.3 g (including an unknown moisture content) was treated as in FIGS. 3 and 4, without shaking. At a weight loss totaling 62.9 g up to arrival at portion 39 of the curve, the break point 38 was situated at a weight loss of 15.4 g. From this it is found that the sample contained 15.4 g corresponding to 1.19 wt.-% of moisture or water, and 62.9−14.4=47.5 g corresponding to 3.66 wt.-% of binder. The air was fed at a rate of about 1,500 l/h. The analysis was discontinued after twenty minutes since no further weight loss could be detected. The result of the analysis agreed with the abovestated binder content of 3.8 wt.-% with an accuracy sufficient for practical applications.

It will be understood that each of the elements described above, or two or more together, may also find a useful application in other types of methods and constructions differing from the types described above.

While the invention has been illustrated and described as embodied in a method and apparatus for determining the binder content of bituminous building materials, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of determining the binder content of bituminous building material including a mixture of a mineralic constituent, a bituminous binder and moisture comprising the steps of: preparing a sample of said material; heating the sample to a temperature between 300° to about 550° C. to thermally remove the moisture and the binder without substantially decomposing the other constituents of the mixture; cooling the sample after the thermal removal of the binder, and subsequently weighing the sample; generating during said heating step a curve which reflects total weight loss of the sample in relation to time; ending the heating step when the curve shows that removal of the moisture and decomposition of the binder has substantially ended; taking from the curve a break point which shows up to which time the weight loss is substantially due to the removal of moisture from the sample and from which time the weight loss is substantially due to a decomposition of the binder; and determining the binder content of the sample from the difference between the total weight loss of the sample and the weight loss of the sample at the break point.

2. A method according to claim 1, wherein the sample is cooled to ambient temperature after the heating step.

3. A method of determining the binder content of bituminous building material including a mixture of a mineralic constituent, a bituminous binder and moisture comprising the steps of: preparing a sample of said material; predrying the sample at a temperature of 200°-300° C.; heating the sample to a temperature between 300° to about 550° C. to thermally remove the residual moisture and the binder without substantially decomposing the other constituents of the mixture; generating during said heating step a curve which reflects total weight loss of the sample in relation to time; ending the heating step when the curve shows that removal of the moisture and decomposition of the binder has substantially ended; taking from the curve a break point which shows up to which time the weight loss is substantially due to the removal of moisture from the sample and from which time the weight loss is substantially due to a decomposition of the binder; and determining the binder content of the sample from the difference between the total weight loss of the sample and the weight loss of the sample at the break point.

4. A method according to claim 3, wherein the sample is cooled after the heating step.

5. A method according to claim 3, wherein the sample is cooled to ambient temperature after the heating step.

* * * * *